US00PP35336P2

(12) United States Plant Patent
Read

(10) Patent No.: US PP35,336 P2
(45) Date of Patent: Aug. 22, 2023

(54) ***LEUCANTHEMUM* PLANT NAMED 'REAL TINY BUBBLES'**

(50) Latin Name: ***Leucanthemum* x *superbum***
Varietal Denomination: Real Tiny Bubbles

(71) Applicant: Charles Richard Read, Bognor Regis (GB)

(72) Inventor: Charles Richard Read, Bognor Regis (GB)

( * ) Notice: Subject to any disclaimer, the term of this patent is extended or adjusted under 35 U.S.C. 154(b) by 0 days.

(21) Appl. No.: 18/088,662

(22) Filed: Dec. 26, 2022

(51) Int. Cl.
*A01H 5/02* (2018.01)
*A01H 6/14* (2018.01)

(52) U.S. Cl.
USPC ..... Plt./287
CPC ..... *A01H 6/14* (2018.05)

(58) Field of Classification Search
USPC ..... Plt./287
CPC ..... A01H 6/14; A01H 5/02
See application file for complete search history.

*Primary Examiner* — Keith O. Robinson
(74) *Attorney, Agent, or Firm* — Weatherly IP Solutions, LLC; James M. Weatherly

(57) ABSTRACT

A new cultivar of *Leucanthemum* plant named 'Real Tiny Bubbles' that is distinguishable by tight clumping basal branching and upright plant habit, uniformly long and narrow leaves, inflorescences which first open to display white tubular ray florets and yellow disc florets, and maturing to exhibit only the ray florets arranged as a hemispherical terminal inflorescence in which the disc florets are entirely obscured. Flowering of 'Real Tiny Bubbles' commences in April and continues until October on plants which are 32 cm in height (including the inflorescences) and 40 cm in diameter at maturity.

2 Drawing Sheets

Figure 1:
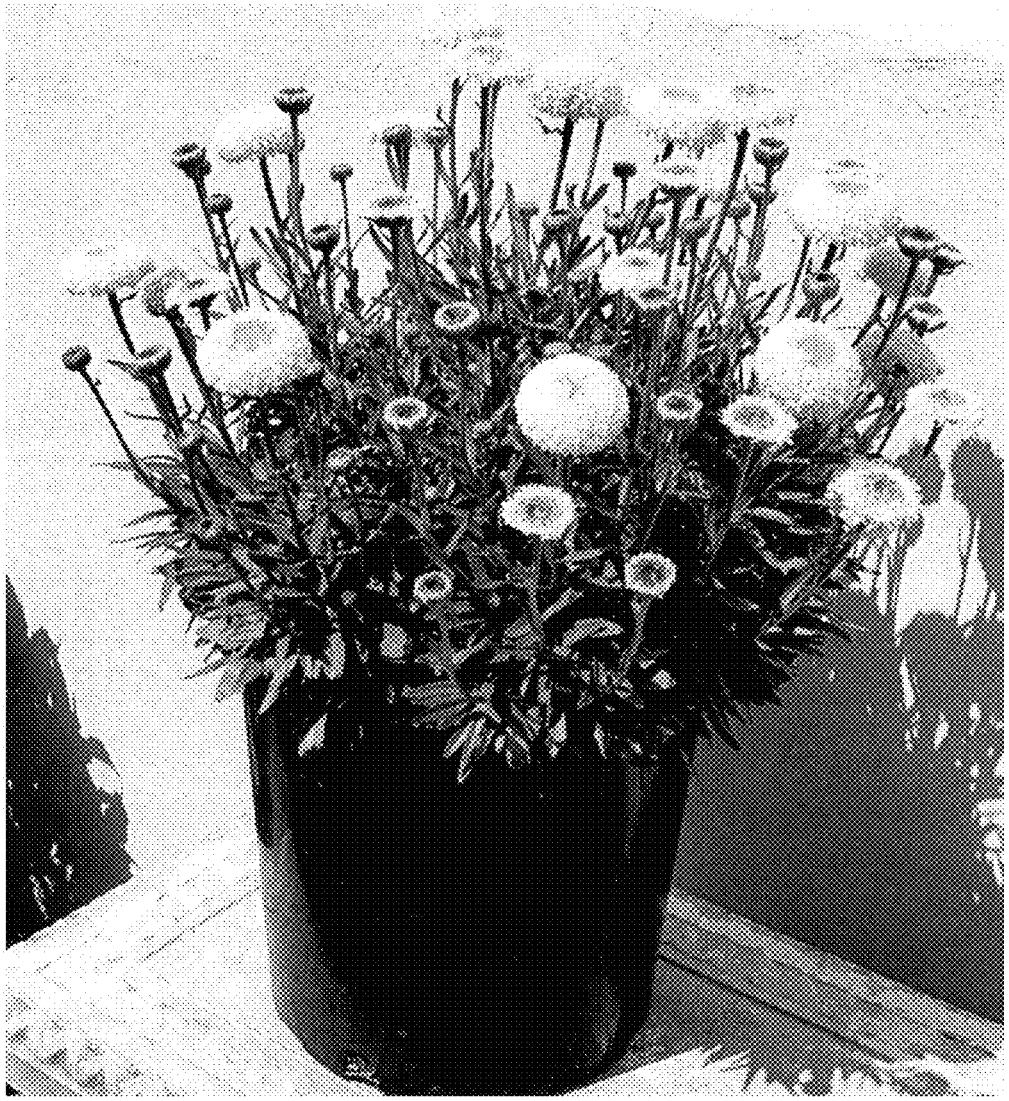

Genus and species: *Leucanthemum* x *superbum*.
Variety denomination: 'Real Tiny Bubbles'.

BACKGROUND OF THE NEW PLANT

The present invention relates to a new and distinct cultivar of *Leucanthemum* commonly known as Shasta daisy, which is grown as an ornamental plant for use in the garden and landscape. The new cultivar is known botanically as *Leucanthemum* x *superbum* and will be referred to hereinafter by the cultivar name 'Real Tiny Bubbles'.

*Leucanthemum* is a genus within the family Asteraceae in which the commonly referred to "flower" is botanically the inflorescence which is comprised of outer showy ray florets surrounding smaller disc florets.

'Real Tiny Bubbles' arose and was selected from an ongoing breeding program which is conducted by the inventor at the inventor's nursery in West Sussex, United Kingdom. The breeding program commenced in 2006 with the aim of developing new and improved commercial varieties of *Leucanthemum*. Each year's breeding cycle consists of controlled pollination between chosen male and female parents including unnamed and unreleased seedlings retained from previous breeding cycles. Seed from each year's cycle is harvested and sown in the fall, and new seedlings are raised and evaluated in the following summer.

'Real Tiny Bubbles' is a seedling selection that resulted from the controlled pollination in 2011 of a single plant of the inventor's proprietary *Leucanthemum* seedling code L1411-3 (unreleased and unpatented) as the female parent, using pollen from a single plant of the inventor's proprietary *Leucanthemum* seedling code L1750-10 (unreleased and unpatented) as the male parent. The inventor selected 'Real Tiny Bubbles' in 2019 for its combination of tight clumping basal branching and upright habit, and domed to hemispherical inflorescences which are pure white in color and held on strong flower stems.

'Real Tiny Bubbles' was first asexually propagated by the inventor in West Sussex, United Kingdom in 2020 using the method of vegetative division and subsequently by basal shoot cuttings. Since that time under careful observation 'Real Tiny Bubbles' has been determined uniform, stable and true to type in subsequent generations of asexual propagation.

SUMMARY

The following traits have been repeatedly observed and represent the distinguishing characteristics of 'Real Tiny Bubbles'. In combination these traits set 'Real Tiny Bubbles' apart from all other existing varieties of *Leucanthemum* known to the inventor. 'Real Tiny Bubbles' has not been tested under all possible conditions and phenotypic differences may be observed with variations in environmental, climatic, and cultural conditions, however, without any variance in genotype.

1. 'Real Tiny Bubbles' exhibits a tight clumping basal-branching and an upright plant habit.
2. A mature plant of 'Real Tiny Bubbles' growing in a 3.7 gallon container, or planted in the ground, is 20 cm to 22 cm in height to the top of the foliage mound, and 32 cm in height to the uppermost flowers, and 40 cm in diameter.
3. The leaves of 'Real Tiny Bubbles' are uniformly long and narrow.
4. A fully expanded inflorescence of 'Real Tiny Bubbles' is hemispherical in shape with pure white tubular ray florets which completely envelop and conceal the yellow disc florets.

5. A fully expanded inflorescence of 'Real Tiny Bubbles' consists of approximately 300 white ray florets and 400 yellow disc florets.
6. The ray florets of 'Real Tiny Bubbles' are tubular or quilled in shape with flared free petal lobes.
7. The ray florets of 'Real Tiny Bubbles' are arranged in multiple concentric whorls.
8. Flowering of 'Real Tiny Bubbles' commences in April and continues until October.
9. 'Real Tiny Bubbles' is hardy in USDA Zone 5 (−20° F. or −28° C.).

COMPARISON WITH PARENTAL LINES AND KNOWN VARIETY

In comparison with its parents, both of which bear white flowers, plants of 'Real Tiny Bubbles' are shorter and more compact than its male parent, and bear many more inflorescences than the female parent. In addition, in comparison with both parents, the inflorescences of 'Real Tiny Bubbles' comprise many more ray florets arranged in a dense hemispherical cluster which conceals the disc florets.

The commercial variety of *Leucanthemum* which the inventor considers to most closely resemble 'Real Tiny Bubbles' is *Leucanthemum* Plant Named 'REAL COMET' (U.S. Plant Pat. No. 33,626). Both varieties 'Real Tiny Bubbles' and 'REAL COMET' exhibit tight clumping basal branching habits with narrow serrated foliage. However, the inflorescences of 'Real Tiny Bubbles' are hemispherical in shape, concealing the disc florets. The inflorescences of 'REAL COMET' are cushion-shaped and open.

BRIEF DESCRIPTION OF THE PHOTOGRAPHS

The accompanying color photographs illustrate the overall appearance of 'Real Tiny Bubbles' showing the color of foliage and inflorescence as true as is reasonably possible to obtain in color reproductions of this type. The illustrated plant has been grown without any pruning or use of chemical growth regulators. The colors in the photographs may differ from color values cited in the detailed botanical description, which accurately describe the actual color of 'Real Tiny Bubbles'.

FIG. 1 illustrates a four year old plant of 'Real Tiny Bubbles' which has been grown outdoors in a 3.7 gallon container in Santa Barbara, Calif. The photograph was taken in April 2022 and the illustrated plant is approaching full flower.

Figure 2:
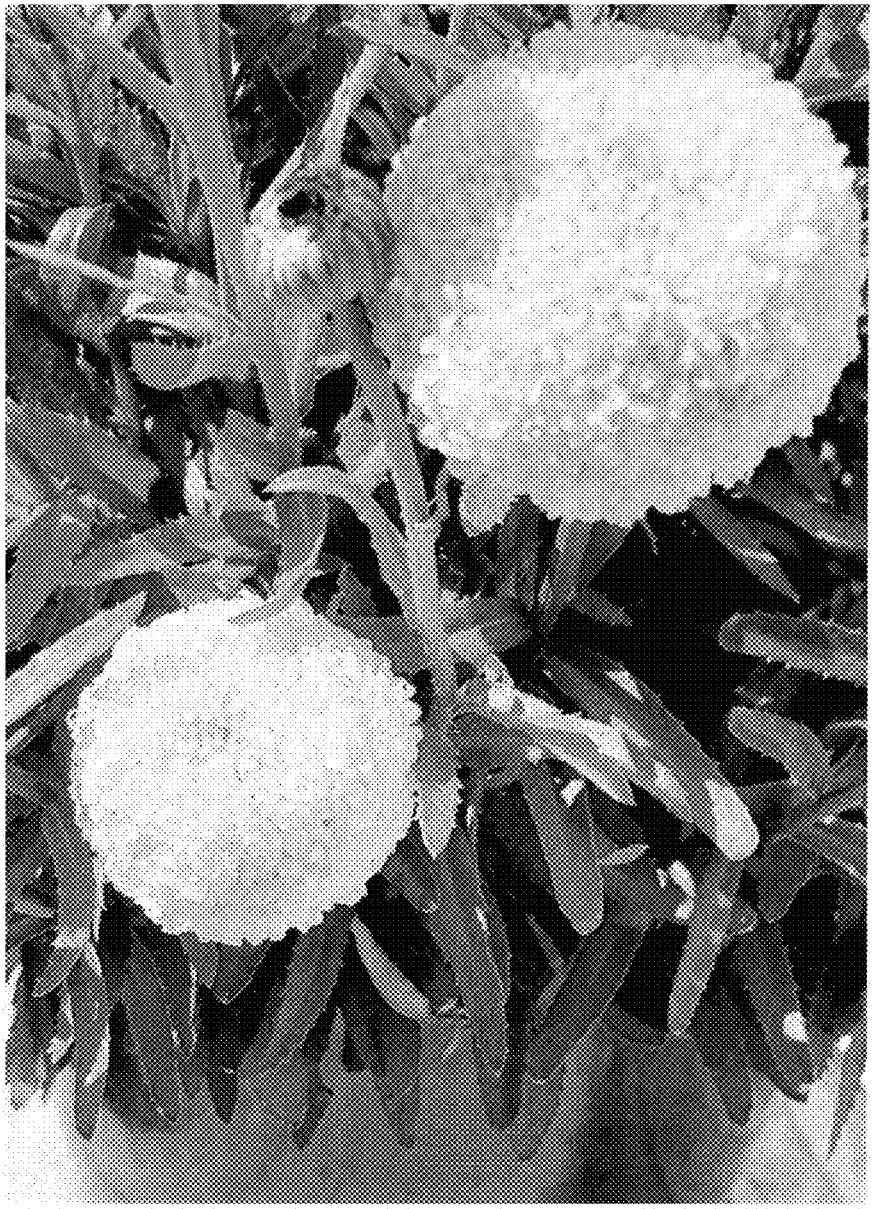

FIG. 2 presents a close-up view of the fully developed inflorescence of 'Real Tiny Bubbles'. The ray florets have entirely enveloped the disc florets.

BOTANICAL DESCRIPTION OF THE PLANT

The following is a detailed botanical description of the new cultivar 'Real Tiny Bubbles'. Observations, measurements, values and comparisons were collected in Santa Barbara, Calif. during April 2022, from a 4-year-old plant growing outdoors in 3.7-gallon container. Color determinations are made in accordance with The 2007 Royal Horticultural Society Colour Chart from London, England, except where general color terms of ordinary dictionary significance are used.

Botanical classification:

*Family*.—Asteraceae (formerly Compositae).

*Genus*.—*Leucanthemum*.

*Species*.—x *superbum*.

*Denomination*.—'Real Tiny Bubbles'.

*Common name*.—Shasta daisy.

*Habit*.—Vigorous basal-branching upright growth habit.

*Commercial category*.—Perennial.

*Use*.—For garden and landscape.

*Suggested commercial container size*.—4-inch, 1 gallon, 2-gallon containers. Larger containers may be used for producing specimen or display plants.

*Parentage*.—*Leucanthemum* x *superbum* 'Real Tiny Bubbles' is a seedling selection resulting from the controlled cross-pollination of the following parents: Male parent: inventor's proprietary *Leucanthemum* seedling code L1750-10. Female parent: inventor's proprietary *Leucanthemum* seedling code L1411-3.

*Propagation method*.—Basal shoot cuttings, division and tissue culture.

*Rooting system*.—Fine and fibrous.

*Vigor*.—Vigorous.

*Time to develop roots* (*range*).—14 to 20 days are needed for an initial cutting to develop roots.

*Temperature to develop roots* (*range*).—The recommended air temperature is 20° C. to 21° C.

*Crop time* (*range*).—7 to 8 months to produce a flowering plant in a 1 gallon container starting from a rooted cutting. 10 months to produce a full plant in a 2 gallon container.

*Plant dimensions* (*one year*).—40 cm in height and 35 cm in width.

*Cultural requirements*.—Grow in full sun and rich, moist moderately fertile well-draining soil.

*Pest or disease resistance and susceptibility*.—No specific disease or pest resistance or susceptibility has been observed or is known to the inventor.

*Hardiness*.—USDA Zone 5.

Stems, branches: All basal stems originate from underground and bear secondary branches above ground. All stems and branches bear terminal inflorescences.

*Quantity*.—Approximately 75 basal stems and secondary branches.

*Stem length*.—20 cm to 32 cm.

*Stem diameter*.—3 mm to 4 mm, becoming wider 4 mm to 5 mm beneath inflorescence.

*Stem shape*.—Terete with longitudinal parallel ridges approximately 0.5 mm to 1 mm apart.

*Stem surface*.—Glabrous.

*Stem color*.—138B.

*Stem strength*.—Strong and stiff.

Foliage:

*Type* (*division*).—Simple.

*Arrangement*.—Alternate.

*Attachment*.—Sessile.

*Internode length*.—Ranges between 3 mm and 16 mm.

*Margin*.—Serrate, 10-12 teeth spaced at 3 mm-8 mm intervals, depth 1 mm.

*Apex*.—Acute.

*Base*.—Truncate, clasping.

*Leaf dimensions* (*fully developed*).—75 mm in length, 13 mm in width.

*Leaf color*.—Adaxial surface 137B, abaxial surface 137D.

*Leaf shape*.—Lanceolate.

*Leaf venation*.—Pinnate, adaxial midrib depressed, abaxial midrib raised, approximately 0.5 mm above abaxial leaf surface.

*Vein color* (*both surfaces*).—Same as leaf.

*Leaf surface* (*both surfaces*).—Glabrous, semi-glossy.

Inflorescence:

*Inflorescence type*.—Capitulum, consisting of outer ray florets, inner ray florets, and disc florets.

*Inflorescence shape*.—Initially shallow cylindrical becoming hemispherical when ray florets are fully developed and have enveloped the disc florets.

*Inflorescence quantity per plant*.—Approximately 75, of which 30 are at bud (no ray florets visible) stage and 45 are open and showing ray florets inflorescences in varying stages of development.

*Inflorescence diameter* (*maximum*).—50 mm.

*Inflorescence height*.—12 mm when ray florets first visible, 30 mm when ray florets fully developed and inflorescence is hemispherical.

*Inflorescence aspect*.—Upright.

*Inflorescence colors* (*when fully developed*).—Outer ray florets: NN155B to NN155D. Inner ray florets (nearest to disc) ray florets: NN155A to 155A. Central disc: 17A.

*Fragrance*.—Slightly musty.

*Blooming season*.—April to October.

*Lastingness of inflorescence* (*range*).—10 to 14 days on the plant, ray florets are persistent.

Bud:

*Bud dimensions* (*prior to first showing of ray florets*).—9 mm in height and 16 mm in diameter.

*Bud shape*.—Flattened sphere.

*Bud color*.—147B.

*Bud surface*.—Glabrous.

Ray florets:

*Ray floret arrangement*.—Whorled, consisting of 7-9 concentric whorls of primary outer ray florets and 5-6 whorls of smaller inner ray florets nearest the disc.

*Shape*.—Tubular, quilled, corolla tube consisting of 5 fused petals with free petal lobes.

*Quantity per inflorescence*.—120 outer ray florets, 180 inner ray florets.

*Outer ray florets*.—Corolla tube: 13 mm in length, 5 mm-9 mm in diameter. Color: NN155B to NN155D. Surface (both): Glabrous, glossy. Peduncle: 6 mm in length, 1 mm in diameter, smooth, color 144C-144D.

*Inner ray florets*.—Corolla tube: 7 mm in length, 4 mm in diameter. Color: NN155A to 155A. Surface (both): Glabrous, glossy. Peduncle: 4 mm in length, 0.75 mm in diameter, smooth, color 144C-144D.

Ray floret petals:

*Outer ray floret petals*.—Number: 5 petals fused longitudinally to form corolla tube. Shape: Rectangular, then terminating in thin strap-like petal lobes. Dimensions (fused section): 13 mm in length, 2 mm in width. Dimensions (free petal lobes): 4 mm-5 mm in length, 1.5 to 2.5 mm in width. Petal lobe aspect: Outwardly reflexed or recurved. Petal lobe apex: Rounded, occasionally emarginate where petals fused. Petal lobe margin: Entire. Petal color (both surfaces): NN155B to NN155D.

*Inner ray florets*.—Number: 5 petals fused longitudinally to form corolla tube. Shape: Rectangular, then terminating in thin strap-like petal lobes. Dimensions (fused section): 7 mm in length, 1.5 mm in width. Dimensions (free petal lobes): 2 mm in length, 1.0 to 1.5 mm in width. Petal lobe aspect: Outwardly reflexed or recurved. Petal lobe apex: Rounded, occasionally emarginate where petals fused. Petal lobe margin: Entire. Petal color (both surfaces): NN155A to 155A.

Disc floret:

*Disc diameter*.—2.5-3.0 cm.

*Disc floret quantity*.—Approximately 400 per inflorescence, massed at center of receptacle.

*Disc floret color*.—17A.

*Disc floret shape*.—Tubular, consisting of five fused petals and free and flared petal lobes.

*Disc floret tube dimensions*.—5 mm-6 mm in length, 1 mm in diameter.

*Disc floret lobe dimensions*.—2 mm in length, 1 mm in diameter.

*Disc floret corolla tube*.—Color 17A.

*Disc floret petal apex*.—Acute.

*Disc floret petal base*.—Truncate.

*Disc floret peduncle*.—3 mm-4 mm in length, 0.75 mm in diameter, smooth, color 144C to 144D.

Involucral bracts:

*Arrangement*.—Tightly held against and beneath inflorescence base, occasionally protruding through the inflorescence and presenting dark brown to black apices.

*Quantity* (*average*).—120 per inflorescence, overlapping, fused at base.

*Shape*.—Short lanceolate.

*Dimensions*.—5 mm-6 mm in length, 2 mm in width.

*Texture*.—Fleshy base, translucent paper-like apex with fine ciliate margins.

*Bract color* (*fleshy base, both surfaces*).—138B.

*Bract color* (*towards and at apex, both surfaces*).—200C.

*Bract apex*.—Rounded.

*Bract apex cilia*.—1 mm-2 mm in length, fine, color 200C.

*Bract base*.—Truncate.

*Bract surface* (*both surfaces*).—Glabrous except ciliate apex.

*Bract margin*.—Entire except ciliate apex.

Reproductive organs:

*Ray florets*.—Androecium (stamens, anthers, filaments, pollen): Absent. Pistil: 1, 2 mm in length, hair-like, diameter less than 0.2 mm., color 162C. Stigma: Tripartite, 1.5 mm in length, hair-like, diameter less than 0.2 mm, color 162C. Ovary: Not observed.

*Disc florets*.—Stamens: 5, fine hair-like, reflexed at apex, length 3 mm, diameter less than 0.5 mm, color 17A. Anthers: not visible. Pollen: Slight amount, color 23A. Ovary: Not observed.

Seed: None observed to date.

I claim:

1. A new and distinct cultivar of *Leucanthemum* plant named 'Real Tiny Bubbles' as described and illustrated herein.

* * * * *